United States Patent
Zimpfer et al.

(10) Patent No.: US 9,186,120 B2
(45) Date of Patent: Nov. 17, 2015

(54) INDUCTIVE ROTATING TRANSMISSION DEVICES WITH RIPPLE COMPENSATION FOR COMPUTER TOMOGRAPHS

(75) Inventors: Arno Zimpfer, Mammendorf (DE); Stefan Fischer, Fuerstenfeldbruck (DE)

(73) Assignee: SCHLEIFRING UND APPARATEBAU GMBH, Fuerstenfe Ldbruck (DE)

( * ) Notice: Subject to any disclaimer, the term of this patent is extended or adjusted under 35 U.S.C. 154(b) by 1197 days.

(21) Appl. No.: 13/094,346

(22) Filed: Apr. 26, 2011

(65) Prior Publication Data

US 2011/0261931 A1 Oct. 27, 2011

(30) Foreign Application Priority Data

Apr. 27, 2010 (DE) .................. 10 2010 016 652

(51) Int. Cl.
- *H05G 1/10* (2006.01)
- *A61B 6/00* (2006.01)
- *H02J 5/00* (2006.01)

(52) U.S. Cl.
CPC .. *A61B 6/56* (2013.01); *H02J 5/005* (2013.01)

(58) Field of Classification Search
None
See application file for complete search history.

(56) References Cited

U.S. PATENT DOCUMENTS

| | | | |
|---|---|---|---|
| 6,301,128 B1 * | 10/2001 | Jang et al. | 363/17 |
| 6,548,985 B1 * | 4/2003 | Hayes et al. | 320/108 |
| 7,054,411 B2 | 5/2006 | Katcha et al. | |
| 7,197,113 B1 | 3/2007 | Katcha et al. | |
| 7,212,415 B2 * | 5/2007 | Osaka | 363/21.02 |
| 7,634,046 B2 * | 12/2009 | Krumme | 378/19 |
| 2009/0276199 A1 * | 11/2009 | Krumme et al. | 703/7 |

FOREIGN PATENT DOCUMENTS

| | | |
|---|---|---|
| CN | 1933284 | 3/2007 |
| CN | 101601107 | 12/2009 |
| DE | 102007006394 | 5/2008 |
| WO | 2008/055664 | 5/2008 |

\* cited by examiner

*Primary Examiner* — Rexford Barnie
*Assistant Examiner* — David Shiao
(74) *Attorney, Agent, or Firm* — Kevin L. Daffer; Daffer McDaniel, LLP

(57) ABSTRACT

A method for compensation of input voltage fluctuations in an inductive rotating coupler is disclosed. This coupler includes a power generator that feeds an alternating-current voltage into a resonance circuit including a resonance capacitor and an inductive rotating transmission device. The power generator is fed with an input direct-current voltage that may fluctuate, for example, owing to residual ripple. A control unit determines this input direct-current voltage and calculates there from an optimum operating frequency for the power generator, so that the output voltage at the load remains constant.

6 Claims, 2 Drawing Sheets

INDUCTIVE ROTATING TRANSMISSION DEVICES WITH RIPPLE COMPENSATION FOR COMPUTER TOMOGRAPHS

PRIORITY CLAIM

This application claims priority to pending German Application No. 102010016652.9 filed on Apr. 27, 2010.

BACKGROUND OF THE INVENTION

1. Field of the Invention

The invention relates to inductive couplers for non-contacting power transmission, in particular to inductive rotating transmission devices and here particularly to inductive rotating transmission devices for computer tomographs. With these, the electrical power substantially needed for driving an X-ray tube is transmitted from a stationary side to a rotating side of a gantry of a computer tomograph. The transmission is here effected without contact by means of an inductive rotary joint that is built up similarly to a transformer in which the primary side and the secondary side are adapted to be rotated with respect to each other.

2. Description of Relevant Art

With units that are rotatable relative to each other, such as radar installations or also computer tomographs, in the same way as with linearly movable units such as crane systems or conveyor vehicles, it is frequently necessary to transmit electrical energy between movable units. In order to transmit this energy without contact, inductive couplers are preferably employed. These have the advantage over mechanical slide tracks or also slip rings that abrasion, wear, mechanical force outlay for moving the coupler, and also outlay of maintenance are substantially less. The term "inductive coupler" here relates to a circuit for generating an alternating current, together with an inductive transformer or rotary joint for energy transmission between two parts that are movable and, in particular, rotatable relative to each other.

Inductive rotating transmission devices as disclosed in U.S. Pat. No. 7,197,113, for example, have magnetic cores of iron or ferrite material and at least one winding on each side of the units that are rotatable relative to each other. An alternating current is fed into a first winding and tapped off via a second winding that is movable relative to the first one.

U.S. Pat. No. 7,054,411 shows a complete circuit of an inductive power transmission system for computer tomographs, together with the associated power electronics.

In DE Publication No. 102007006394, an inductive rotating transmission device is disclosed in which the output voltage is regulated by a control unit which, for this purpose, determines an electrical parameter on the primary winding of the rotating transmission device.

With conductively coupled slip rings it is simple to transmit a predetermined voltage from the stator side to the rotor side. Here only the relatively low ohmic losses need be taken account of. With inductive rotating transmission devices the stray inductance of the rotating transmission device plays a major part. It represents a frequency-dependent impedance that substantially affects the transmission characteristics of the rotating transmission device. This stray inductance depends upon various factors such as the inductance of the windings of the stator side and the rotor side, and also upon the magnetic configuration. Now, in order to transmit electrical energy via a rotating transmission device of this kind, a series capacity is connected in series for compensation. With this, a series resonance circuit results. At its resonance frequency this has an impedance of zero and here makes possible a transmission of high power. For control of the power flux the operating frequency can be chosen to differ from the resonance frequency.

Instead of a series resonance circuit, a parallel resonance circuit also can be constructed by connecting a capacity in parallel. The characteristics described in the following similarly apply to a parallel resonance circuit. At its resonance frequency the resonance circuit has an impedance of almost zero and here makes possible the transmission of high power. By changing the impedance, which is effected by changing the switching frequency, the output voltage can be controlled.

If the arrangement is now operated at a switching frequency that is optimal for certain load conditions, then a conversion of the output voltage at the load results at a certain ratio to the input voltage from the line. In most cases the input voltage from the line is a well-filtered DC (direct-current) voltage that in most cases even originates from a power-factor correcting circuit. However, in some applications a power-factor correcting circuit of this kind is not needed and can be dispensed with. Thus, only a rectified AC (alternating current) from the power line having a relatively high residual ripple is available as an input voltage of the rotating transmission device, which again results in a corresponding residual ripple of the output voltage at the load. In order to reduce the ripple of the voltage at the load, for example the output voltage can be measured and this measured value fed back to the stationary side. With conventional (not movable) power supply units a separate feedback transformer is used for this. However, with rotating transmission devices an additional rotating transmission device is needed, which causes additional cost and requires space.

Alternatively, the filter capacitors on the input side could be enlarged. However, this leads to a large volume of the arrangement and higher cost. Furthermore, the primary-side peak-current consumption from the line increases, whereby the higher harmonics in the line are increased.

Another possibility is to insert an additional converter stage on the rotating side between the secondary side of the rotating transformer and the output. Buck or boost converters are frequently used for these converter stages, but other converters such as Zeta or Ćuk converters are also possible. The input voltage of this downstream converter stage may fluctuate within a wide range with the output voltage being kept constant. However, this solution requires an additional converter on the rotating side, which increases the cost and also the weight, as well as the volume of the arrangement.

SUMMARY OF THE INVENTION

The embodiments are based on the object of developing an inductive coupler means for transmitting electrical energy between two units that are movable relative to each other, in particular an inductive rotating transmission device, in such manner that the output voltage can be kept constant by a primary side control independently from fluctuations of the input voltage. Thus, also the size of a filter capacitor on the input side can be reduced. Another embodiment is a method for maintaining the output voltage of an inductive coupler constant independently from fluctuations of the input voltage. Furthermore, no rotating transmission device shall be needed for transmitting control signals from the secondary side to the primary side for transmitting measured values of the output voltage on the secondary side.

In an embodiment an inductive coupler means preferably an inductive rotating transmission device includes a power generator for generating a pulsed direct-current voltage or an alternating-current voltage. Furthermore, it includes an inductive power transmission means having a primary side and a secondary side which are movable relative to each other. A primary side includes at least one primary winding, and the secondary side includes at least one secondary winding. Furthermore, at least one capacity, preferably in the form of a resonance capacitor, is connected in series with or parallel to the primary winding, so that a series resonance circuit results. Alternatively also, a capacity can be connected in parallel with the primary winding in order to obtain a parallel resonance circuit. The pulsed direct-current voltage or alternating-current voltage of the power generator is fed into this resonance circuit for power transmission, so that an alternating magnetic field arises in the primary winding. This in turn induces a current in the secondary winding, which is passed to a load. Here an optional rectifier with optional smoothing and/or filtering elements may be provided between secondary winding and load. For better coupling between the primary winding and the secondary winding, components including soft magnetic materials, preferably iron or ferrite materials, are provided. Optionally a matching transformer can be provided between the power generator and the inductive power transmission means.

The power generator is fed with a direct current. This direct current can be obtained for example by rectifying and filtering with a charging capacitor from an alternating voltage, for example a line voltage. A control unit is provided for controlling the power generator. This control unit determines the value of the direct current for feeding the power generator and sets the frequency of the power generator accordingly. By changing the frequency of the power generator, the power transfer can be altered via the resonance circuit, because the impedance of the resonance circuit is frequency-dependent. The function also referred to as mathematical function (the relationship) between the frequency of the power generator and the direct current for feeding the power generator is preferably recorded as a calculation formula and/or in a table of values. Optionally this can take account of further parameters such as, for example, the load current. The frequency of the power generator is now set in dependence upon the direct current so that the load voltage at the load is as constant as possible and therewith independent from the direct current. Preferably the adjustment is effected so that the load voltage is also independent from other parameters such as, for example, the load current or also the load voltage.

Preferably the function also referred to as mathematical function connecting the frequency of the power generator and the direct current voltage for feeding the power generator is determined on a model instrument (prototype, operational model, pilot production instrument etc.) and stored in a memory. Alternatively, this function can be also determined in the course of a calibration run.

A method serves for generating a constant output voltage of an inductive coupling means for transmitting electrical energy between two units that are rotatable relative to each other, including a power generator and also an inductive power transmission means and at least one resonance capacity as described above. It includes a sequence of measuring the input direct-current voltage of the power generator; determining a frequency by means of at least one calculation formula and/or table of values in dependence upon the measured input direct-current voltage; and setting the frequency of the power generator to the determined frequency, so that the load voltage at the load is substantially independent from the input direct current.

These steps are preferably performed continuously in this sequence. The repetition frequency of this sequence should be so high that, for example, an input voltage ripple can be precisely scanned and evaluated accordingly. At a line frequency of 50 Hz a repetition frequency of 1000 Hz has proved to be of advantage. Of course, even higher or lower repetition frequencies can be used.

Furthermore, the method can be supplemented by generating a calculation formula and/or table of values which reproduce the function (the relationship) between load voltage and input direct-current voltage.

The result is preferably stored in a memory. The last step is preferably performed prior to the actual operation (the activation) of the inductive coupler means, i.e. prior to the power transmission or even already during a production phase of the instrument or a later calibration phase.

The method is also applicable to inductive rotating transmission devices having a plurality of primary windings and/or a plurality of secondary windings.

Other embodiment is a computer tomograph having an above described inductive coupler means.

For the sake of clarity of presentation, the expositions made in this document relate to inductive rotary joints for energy transmission between units that are rotatable relative to each other, in particular in computer tomographs. However, it will be clear to a person skilled in the art that the same principles may be applied also to any rotating transmission devices and/or also to non-contacting energy transmission between units moving in any desired manner relative to each other, in particular between units that are linearly movable. Here it is merely necessary to perform a conformation of the geometry of the rotary joint to the track and the kind of movement.

The embodiments may be applied here just as advantageously. Basically the embodiments are suitable for inductive coupler means of all power classes. However, it is of special advantage to apply it in power classes of several kilowatts to more than 100 kilowatts.

BRIEF DESCRIPTION OF THE DRAWINGS

In the following the invention will be described by way of example, without limitation of the general inventive concept, on examples of embodiment and with reference to the drawings.

Figure 1:
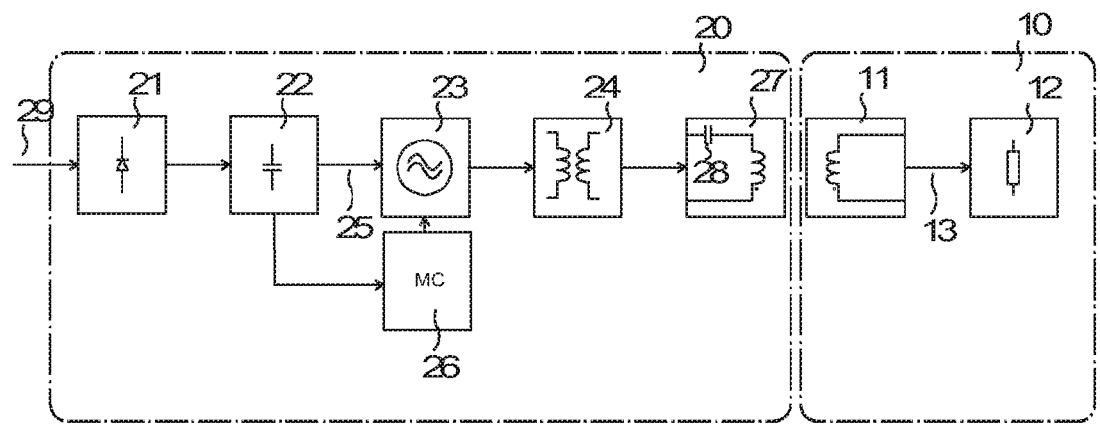
FIG. 1 shows a device in accordance with the invention.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

FIG. 1 illustrates a coupler means for transmitting electrical energy between two units that are movable relative to each other. The stationary part 20 is connected to the rotating part 10 via a rotatable transformer having a primary side 27 and a secondary side 11. The stationary part receives electrical energy via the line input 29. This could be, for example, a 3 phase AC input with 3*400V AC/50 Hz. The input voltage is rectified via the line rectifier 21. One or a plurality of capacitors 22 are disposed downstream of the line rectifier 21 in order to reduce the ripple of the rectified input voltage. The thus smoothed input direct-current voltage 25 is supplied to the power generator 23. The power generator 23 generates an alternating-current voltage or a pulsed direct-current voltage. It preferably includes a circuit stage such as a half-bridge or full-bridge circuit. The pulsed direct-current voltage or alternating-current voltage of the power generator is fed into a resonance circuit in the primary side 27 for power transmission. To match the output voltage or the impedances, an optional matching transformer 24 can be provided. Another advantage of a matching transformer of this kind can be the additional separation of potential. A series capacitor 28 is connected in series with the primary side of the rotatable transformer 27 to form a series resonance circuit. Alternatively also, a parallel capacity can be connected in parallel with the primary winding in order to obtain a parallel resonance circuit. Basically this circuit has a plurality of resonances, but there is only one resonance frequency at which the entire circuit has an extremely low series resistance between the primary side and the secondary side. The transmission of the electrical energy from the primary side 27 to the secondary side 11 can be thus controlled with the switching frequency of the power generator. For better coupling between the primary winding and the secondary winding, components including soft magnetic materials, preferably iron or ferrite materials, are provided. On the rotating part 10, the secondary side of the rotatable transformer 11 supplies a load voltage 13 to the load 12.

A control unit 26, for example in the form of a microcontroller, controls the power generator 23. The control unit determines the value of the input direct-current voltage 25 and sets the frequency of the power generator so that the load voltage 13 is substantially independent from the input direct-current voltage 25. For this, the control unit 26 includes a function and/or a table of values representing the dependence of the frequency upon the measured input direct-current voltage 25. In addition, the control unit can draw on other parameters such as the input current for controlling the power generator. Preferably the function, also referred to as mathematical function connecting the frequency of the power generator and the direct current voltage for feeding the power generator is determined on a model instrument (prototype, operational model, pilot production instrument etc.) and stored in a memory. Alternatively, this function can be also determined in the course of a calibration run.

A method serves for generating a constant output voltage of an inductive coupling means for transmitting electrical energy between two units that are rotatable relative to each other, including a power generator and also an inductive power transmission means and at least one resonance capacity as described above. This method may be performed with the coupler means described above. It may also be applied to any other stationary to rotational coupler. It includes the steps of: a) measuring the input direct-current voltage of the power generator; b) determining a frequency by means of at least one calculation formula and/or table of values in dependence upon the measured input direct-current voltage; c) setting the frequency of the power generator to the determined frequency, so that the load voltage at the load is substantially independent from the input direct current.

The steps (a) to (c) are preferably performed continuously in this sequence. The repetition frequency of this sequence should be so high that, for example, an input voltage ripple can be precisely scanned and evaluated accordingly. At a line frequency of 50 Hz a repetition frequency of 1000 Hz has proved to be of advantage. Of course, even higher or lower repetition frequencies can be used.

Furthermore, the method can be supplemented by: a) generating a calculation formula and/or table of values which reproduce the function (the relationship) between load voltage and input direct-current voltage.

The result is preferably stored in a memory. The last step (d) is preferably performed prior to the actual operation (the activation) of the inductive coupler means, i.e. prior to the power transmission or even already during a production phase of the instrument or a later calibration phase.

The method is also applicable to inductive rotating transmission devices having a plurality of primary windings and/or a plurality of secondary windings.

Figure 2:
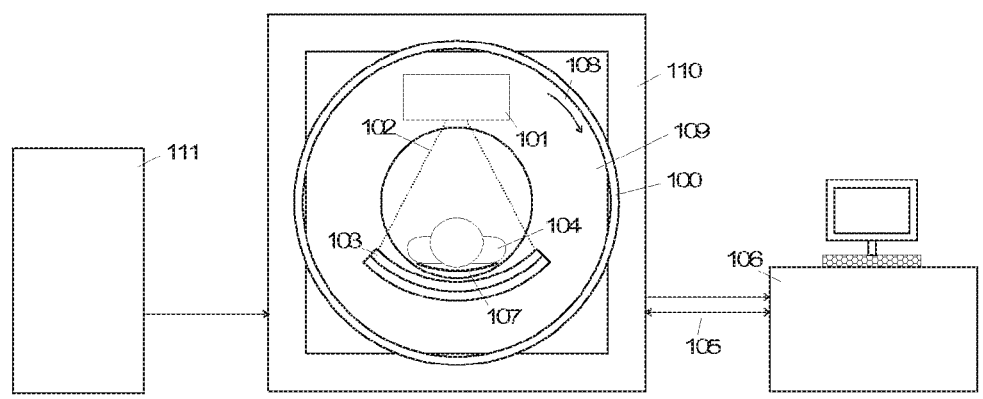
FIG. 2 shows an illustration of principle of a computer tomograph.

FIG. 2 additionally shows schematically the construction of a computer tomograph having an inductive rotating transmission device. The stationary part of the rotating transmission device is suspended within a massive frame 110. The rotating part of the gantry 109 is rotatably mounted with respect to this and rotates along the rotation direction 108. Here is located an X.ray tube 101 for generating an X-ray beam 102 that radiates through a patient 104 lying on a table 107 and is intercepted by a detector 103 and converted to electrical signals. For transmitting the electrical energy from an energy supply unit 111, an inductive power transmission line 100 is provided together with inductive couplers and an inductive rotating transmission device. Here the primary side is disposed on the stationary part and the secondary side on the rotating part. The data obtained by the detector 103 are transmitted to an evaluation unit 106. A control bus 105 serves for this, with which also the gantry itself can be controlled from the evaluation unit.

Figure 3:
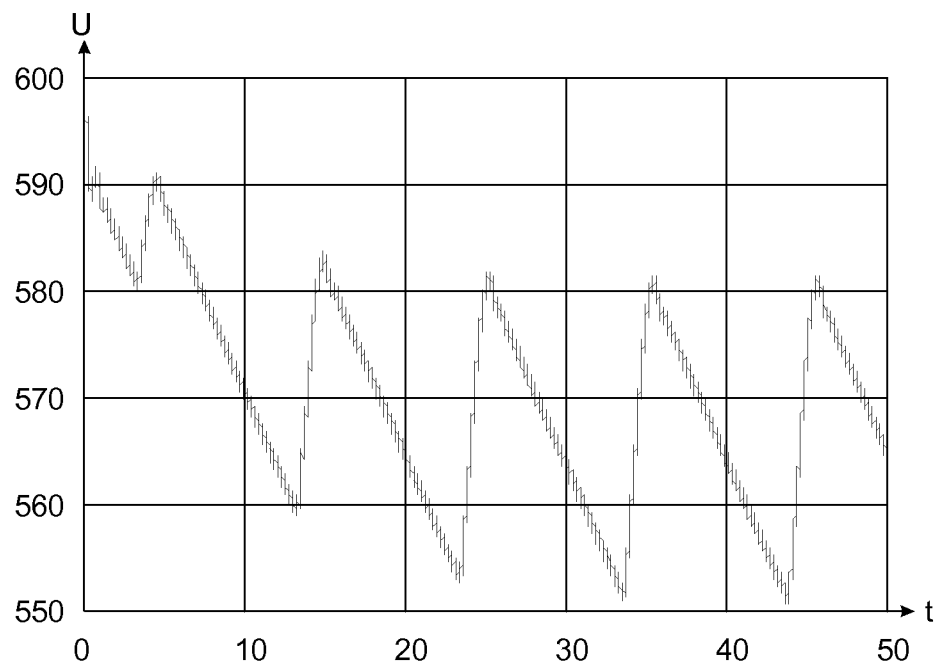
FIG. 3 shows the course of the load voltage according to prior art.

FIG. 3 illustrates the course of the load voltage in accordance with prior art. Here the load voltage U within a range of 550 to 600 volts is plotted during a time t of 0 to 50 milliseconds. Here the ripple of the load voltage having an amplitude of about 30 volts can be clearly discerned.

Figure 4:
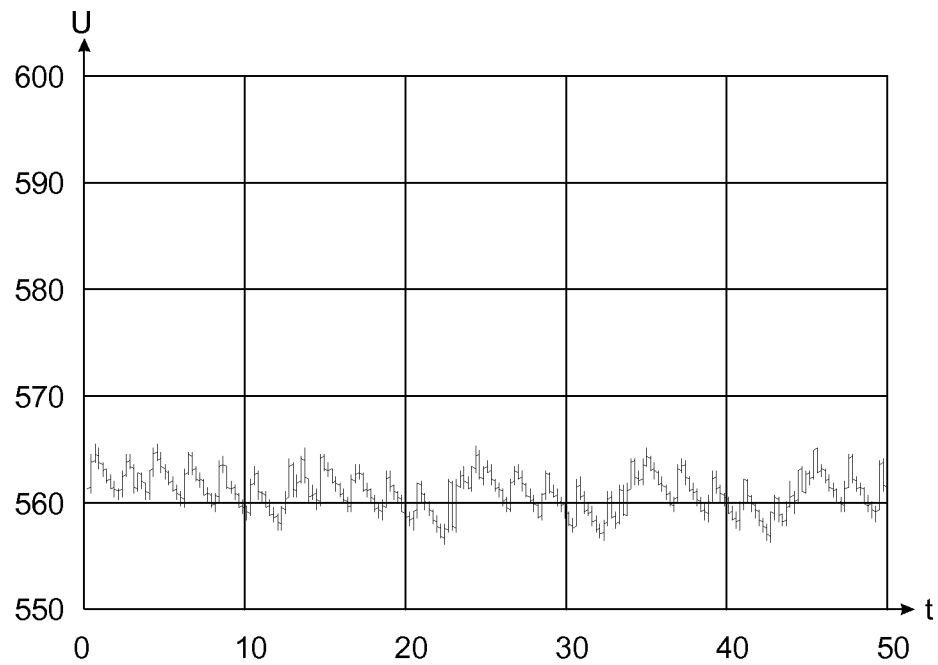
FIG. 4 shows the course of the load voltage according to the invention.

FIG. 4 illustrates the course of the load voltage. The scaling is as in the preceding diagram. With the embodiments the ripple of the load voltage is reduced to an amplitude of about 5 volts. This is a case of only an exemplary illustration with simulated values. According to any concrete embodiment, greater or lesser improvements over prior art may result.

It will be appreciated to those skilled in the art having the benefit of this disclosure that this invention is believed to provide rotary joints and rotating power couplers. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

The invention claimed is:

1. An inductive coupler for transmitting electrical energy between two units that are rotatable relative to each other, including:

a power generator for generating a pulsed DC voltage or an AC voltage from an input DC voltage supplied to the power generator;

at least one resonance circuit having at least one resonance capacitor and an inductive power transmitter having a primary side and a secondary side for coupling the electrical energy between the rotatable units for feeding a load with a load voltage and a load current;

a control unit arranged on the primary side of the inductive power transmitter and coupled for measuring the input DC voltage supplied to the power generator, wherein the control unit maintains at least one of the load voltage and the load current substantially constant by determining and setting a frequency of the power generator in dependence of the input DC voltage, using at least one of a mathematical function and a table of values generated prior to measuring the input DC voltage, and wherein the at least one of the mathematical function and the table of values represent a dependency of the frequency upon the input DC voltage and a relationship between the load voltage and the input DC voltage.

2. The inductive coupler according to claim 1, wherein the control unit draws upon further parameters, which are selected from a group consisting of an input current supplied to the power generator, the load current, and the load voltage, to determine and set the frequency of the power generator.

3. The inductive coupler according to claim 1, wherein the at least one of the mathematical function and the table of values are determined on a model instrument or on the inductive coupler during a calibration run.

4. A method for generating a constant output voltage of an inductive coupler for transmitting electrical energy between two units that are movable relative to each other, the inductive coupler including:

a power generator for generating a pulsed direct current or an alternating current from an input direct-current (DC) voltage supplied to the power generator;

at least one resonance circuit having at least one resonance capacitor and an inductive power transmitter for coupling the electrical energy between the movable units for feeding a load with a load voltage and a load current; and a control unit arranged on the primary side of the inductive power transmitter for determining and setting a frequency of the power generator;

wherein the method comprises:

the control unit measuring the input DC voltage supplied to the power generator; and the control unit maintaining the load voltage or the load current essentially constant by:

determining the frequency of the power generator by means of at least one of a mathematical function and a table of values, which represent a dependency of the frequency upon the measured input DC voltage and a relationship between the load voltage and the measured input DC voltage; and setting the frequency of the power generator to the determined frequency.

5. The method according to claim 4, wherein prior to measuring the input DC voltage, the method further comprises:

generating the mathematical function or the table of values to reproduce the relationship between the load voltage and the input DC voltage.

6. A computer tomograph including at least one inductive coupler for transmitting electrical energy between two units that are rotatable relative to each other, including:

a power generator for generating a pulsed DC voltage or an AC voltage from an input DC voltage supplied to the power generator;

at least one resonance circuit having at least one resonance capacitor and an inductive power transmitter having a primary side and a secondary side for coupling the electrical energy between the rotatable units for feeding a load with a load voltage and a load current;

a matching transformer coupled between the power generator and the at least one resonance circuit for matching impedances there between; and a control unit arranged on the primary side of the inductive power transmitter and coupled for measuring the input DC voltage supplied to the power generator, wherein the control unit maintains at least one of the load voltage and the load current substantially constant by determining and setting a frequency of the power generator in dependence of the input DC voltage, using at least one of a mathematical function and a table of values generated prior to measuring the input DC voltage, and wherein the at least one of the mathematical function and the table of values represent a dependency of the frequency upon the input DC voltage and a relationship between the load voltage and the input DC voltage.

\* \* \* \* \*